United States Patent [19]

Pressman et al.

[11] 4,129,659

[45] Dec. 12, 1978

[54] METHOD FOR IMPROVING CARDIOVASCULAR FUNCTION WITH SALINOMYCIN

[75] Inventors: Berton C. Pressman, Coral Gables; Norberto T. deGuzman, Miami Beach, both of Fla.

[73] Assignee: The University of Miami, Miami, Fla.

[21] Appl. No.: 823,045

[22] Filed: Aug. 8, 1977

[51] Int. Cl.² ............................................. A61K 31/35
[52] U.S. Cl. .................................................... 424/283
[58] Field of Search ......................................... 424/283

[56] References Cited

U.S. PATENT DOCUMENTS

| | | | |
|---|---|---|---|
| 3,857,948 | 12/1974 | Tanaka et al. | 424/283 |
| 3,873,715 | 3/1975 | Pressman et al. | 424/283 |
| 3,985,893 | 10/1976 | Holland et al. | 424/272 |

*Primary Examiner*—Donald B. Moyer
*Attorney, Agent, or Firm*—Burns, Doane, Swecker & Mathis

[57] ABSTRACT

A method is disclosed for improving cardiovascular function which comprises administering an effective amount of the carboxylic ionophore salinomycin.

12 Claims, No Drawings

METHOD FOR IMPROVING CARDIOVASCULAR FUNCTION WITH SALINOMYCIN

The invention described herein was supported in part in the course of work under a grant from the Department of Health, Education and Welfare.

BACKGROUND OF THE INVENTION

1. Field of the Invention

Although many cardiovascular agents are known today, there continues to be a demand for new, improved therapeutic entities. One problem in current cardiovascular therapy is that during the management of cardiogenic shock agents presently used generally have undesirable excessive chronotropic effects and have a short biological half-life requiring constant infusion in a clinical setting for effective treatment. The present invention discloses a new cardiovascular agent and is concerned with a method for using said agent in treating cardiac and coronary insufficiency in warm blooded mammals and is more particularly concerned with methods for increasing the contractility of mammalian heart muscle and increasing the coronary flow by administering an effective amount of the microbially produced salinomycin.

2. Discussion of the Prior Art

The successful management of various cardiac insufficiencies such as shock, particularly cardiogenic shock, congestive heart failure or myocardial infarction resulting from acute and chronic trauma to the myocardium has been sought by the use of various therapeutic entities among which can be mentioned dopamine which exerts positive inotropic and chronotropic effects. More recently a new class of therapeutic agents known as ionophores have been shown to exert positive inotropic effects on cardiac muscle. Ionophores are compounds that possess the ability to move ions across membranes. Among the ionophores which have been shown to possess this property are those classified as carboxylic ionophores. U.S. Pat. No. 3,873,715 discloses the antibiotic X-537A (lasalocid), a carboxylic ionophore, and its cardiotrophic properties. Other carboxylic ionophores and descriptions of their cardiotrophic properties are disclosed in U.S. Pat. No. 3,985,893; in the paper *Biological Applications of Ionophores* by Pressman in the Annual Review of Biochemistry, 45, 501–530 (1976); in the paper *New Ionophores for Old Organelles* by Pressman and de Guzman in the Annals of the New York Academy of Sciences, 227, 380–391 (1974); in the paper *Properties of Ionophores with Broad Range Cation Selectivity* by Pressman in Federation Proceedings, 32, (6), 1698–1703 (1973); in Abstract 159 of the Abstracts of the 48th Scientific Sessions, Supplement II to Circulation, 52, October 1975, and in Abstracts of the 42nd Annual Scientific Assembly, American College of Chest Physicians, 70, (3), 424 (1976).

DESCRIPTION OF THE INVENTION

The present invention provides a method for increasing the contractility of mammalian heart muscle and for increasing coronary flow which comprises the administration of an effective amount of the carboxylic ionophore salinomycin.

Salinomycin, its preparation and antimicrobial properties, has been disclosed in U.S. Pat. No. 3,857,948 and in British Pat. No. 1,378,413. It is prepared by culturing *Streptomyces albys* 80,614. A sample of the microorganism has been deposited at the American Type Collection in Rockville, Md., and assigned the number ATCC 21,838.

The structure of salinomycin and its properties have also been described by Kinashi, et al, Tetrahedron Letters, 49, 4955–4958 (1973) and Miyasaki, et al, The Journal of Antibiotics, 27, (11), 814–821 (1974).

Salinomycin has the structure.

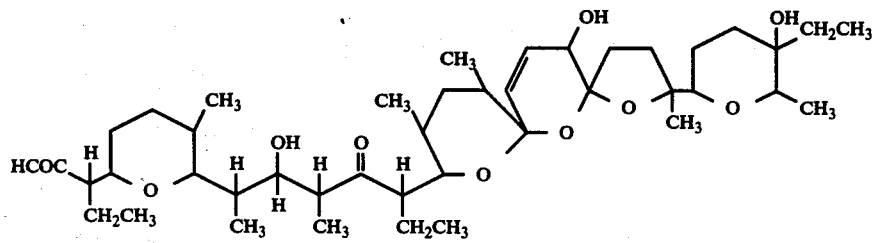

We have now found that salinomycin, in addition to its antibiotic properties, possesses valuable cardiotrophic properties. Studies of salinomycin in anesthetized normal and infarcted dogs and isolated guinea pig and rabbit hearts shows that salinomycin increases the force of myocardial contraction and heart rate, dilates the coronary arteries and decreases the total peripheral resistance resulting in increases in cardiac output, coronary flow and myocardial work efficiency.

Salinomycin also causes an increase in intra-cellular $Na^+$ in exchange for $K^+$ thereby presumably increasing intracellular $Ca^{++}$ in exchange for $Na^+$ as in the commonly accepted mode of action for the cardiac glycosides.

We have also found that salinomycin when compared with other carboxylic ionophores shows a more pronounced separation between the two principal cardiotonic responses of positive inotropy and coronary vasodilation.

It is therefore an object of the present invention to provide a method for increasing the contractility of mammalian heart muscle and coronary flow. Another object is to provide a method for improving the contractility of mammalian heart muscle and increasing coronary flow by administering an effective amount of salinomycin. A still further object is to provide a method for improving the contractility of mammalian heart muscle and increasing coronary flow with minimal side effects. Additional objects of the invention will be apparent to one skilled in the art from the description which follows.

DETAILED DESCRIPTION OF THE INVENTION

The cardiovascular effects of salinomycin are manifested by positive inotropic effects with minimal chronotropic effects. Normal female mongrel dogs, weighing 30-35 lbs., were anesthetized with intravenous sodium pentobarbital (20 mg/kg.) and artificially ventilated. Catheters were introduced through the femoral vessels to the left ventricular cavity of the heart, the thoracic aorta and the inferior vena cava, for the measurement of left ventricular and aortic pressures, and drug administration, respectively. The derivative of the left ventricular pressure (dP/dt) was obtained from a Millar micromanometer-tipped catheter after differentiation by an appropriate R-C circuit. The electrocardiogram was monitored from standard leads attached to the extremities of the dog. All parameters were recorded simultaneously and continuously by a multichannel photographer recorder, and were monitored during the experiments by a multichannel oscilloscope.

After all vital parameters had become stable, 0.03 mg/kg of salinomycin in absolute ethanol was administered over a period of 30 seconds to 1 minute. An hour later a larger dose of 0.06 mg/kg was administered to the same dog. The effects on the coronary flow and on the derivative of the left ventricular pressure, dP/dt, are summarized in Table 1

Table 1
Hemodynamic Effects of Salinomycin

| Dose mg/kg | Coronary Flow % of Control | dP/dt % of Control |
|---|---|---|
| 0.03 | 175% | 131% |
| 0.06 | 375% | 180% |

Further information on the hemodynamic effects of salinomycin were obtained in a study involving seven dogs. Using the same procedure set forth hereinabove and after all vital parameters had become stable, 0.075 mg/kg of salinomycin in absolute ethanol was administered over a period of 30 seconds to one minute. The data is summarized in Table 2.

Table 2
Hemodynamic Effects of Salinomycin[1]

| | Control (mean ± SE) | + Salinomycin (mean ± SE) | Mean % Control | P[2] Value |
|---|---|---|---|---|
| Heart Rate (min.$^{-1}$) | 152 ± 7 | 170 ± 4 | 113 | <.01 |
| dP/dt Max. (mm. Hg sec$^{-1}$) | 2340 ± 265 | 4700 ± 618 | 204 | <.001 |
| Aortic Pressure (mm Hg) | 106 ± 9 / 85 ± 8 | 162 ± 14 / 126 ± 12 | 153 / 148 | <.001 |
| Cardiac Output (L/min) | 1.83 ± .2 | 3.2 ± .2 | 178 | <.001 |
| Total Peripheral Resistance (dynes sec cm$^{-5}$) | 4200 ± 600 | 3200 ± 400 | 77 | <.02 |
| Coronary Flow (ml/min) | 21 ± 4.8 | 93 ± 19 | 522 | <.01 |
| Coronary Resistance (dynes sec cm$^{-5}$) | 460 ± 98 | 150 ± 25 | 38 | <.01 |

[1]hemodynamic effects at dose that doubles left ventricular max. dP/dt; 0.075 mg/kg in absolute ethanol.
[2]Based on Student's paired "t" test.

Extended experimental studies were conducted involving a number of ionophores. A comparison of their effects yielded the data which is summarized in Table 3.

Table 3
Summary of Physiological Effects of Ionophores[1]

| | 1 | 2 | 3 | 4 | 5 | 6 |
|---|---|---|---|---|---|---|
| Ionophore | Inotropic Potency[2] | Coronary Flow Potency[3] | Ratio 2/1 | RBC K$^+$ Leak Potency[4] | Ratio 1/4 | Ratio 2/4 |
| Lasalocid | 1.0 | 1.0 | 1.0 | 1.0 | 1.0 | 1.0 |
| Lysocellin | 1.5 | — | — | 4.1 | .36 | — |
| Septamycin | 2.0 | — | — | — | — | — |
| Nigericin | 2.8 | 3.4 | 1.2 | 16.4 | .17 | .21 |
| Dianemycin | 4.3 | 4.6 | 1.1 | 18.0 | .24 | .25 |
| Monensin | 6.1 | 10.0 | 1.6 | 7.2 | .84 | 1.4 |
| X-206 | 7.7 | 8.6 | 1.1 | 10.9 | .70 | .79 |
| Salinomycin | 12.1 | 19.6 | 1.6 | 10.0 | 1.21 | 1.96 |
| A-204 | 13.1 | 14.1 | 1.1 | 41.0 | .32 | .34 |

[1]Studies conducted on anesthetized dogs.
[2]Ionotropic potencies are expressed as the reciprocal of the dose required to double dP/dt Max., relative to the dose of Lasalocid required to double dP/dt Max.
[3]Coronary flow potency is calculated as the inotropic potency, normalized for coronary flow by the factor: coronary flow increased produced by doubling dose of the test ionophore/coronary flow produced by the doubling dose of Lasalocid.
[4]RBC K$^+$ leak potency is the reciprocal of the concentration which leaked 15 mMK$^+$/hr. from the erythrocytes of whole fresh human blood, relative to that of Lasalocid. The reference concentration of Lasalocid was 11.5 μM.

Although the data summarized in Table 3 shows that the ionophore A-204 has a slightly higher inotropic potency than salinomycin, A-204 has a markedly reduced coronary flow potency than salinomycin and exhibits a 400% increase in the undesirable potassium cellular leakage potency. Excessive rise in plasma potassium normally suppresses cardiac contractility hence it is desirable to hold the ratio of plasma potassium rise: desired pharmacological effects to a minimum. The intrinsic ability of the test ionophores to release cellular potassium was measured using whole human blood and assaying the release of erythrocyte potassium into the plasma fraction in vitro. By this criterion (Table 3, columns 5 and 6) salinomycin is superior to all other carboxylic ionophores examined. Moreover, it has been shown that A-204 exhibits the undesirable side effects of skeletal and cardiac myopathy upon chronic administration. This undesirable effect has not been shown by salinomycin.

The invention further provides pharmaceutical compositions, comprising as active ingredient salinomycin, the pharmaceutically acceptable sodium or potassium salt thereof or a water soluble lyophilized salinomycin - human serum albumin preparation in association with a pharmaceutical carrier or excipient. The composition can be presented in a form suitable for oral, parenteral, or intracardiac administration. Thus, for example, compositions for oral administration are solid or liquid and can take the form of capsules, tablets, coated tablets, suspensions, etc, employing such carriers or excipients conventionally used in the pharmaceutical art. Suitable tableting excipients include lactose, potato and maize starches, talc, gelatin and stearic and silicic acids, magnesium stearate and polyvinylpyrrolidone.

For parenteral administration, the carrier or excipient can be a sterile, parenterally acceptable liquid, e.g., water, or a parenterally acceptable oil, e.g., arachis oil, contained in ampoules.

The free acid form of salinomycin and the pharmaceutically acceptable sodium and potassium salts which can also be used in practicing the present invention have minimal solubility in water. When used in this form a solution of salinomycin in an acceptable organic solvent, e.g., absolute ethanol, is preferably employed.

A water soluble salinomycin preparation can be prepared by absorbing salinomycin on human serum albumin and lyophilizing the material. The lyophilized solid can then be dissolved in a suitable pharmaceutically acceptable carrier such as sterile water or saline to form a solution suitable for oral or parenteral administration.

Advantageously, the compositions are formulated as dosage units, each unit being adapted to supply a fixed effective dose of salinomycin, the pharmaceutically acceptable sodium or potassium salt thereof or a water lyophilized salinomycin - human serum albumin preparation. Although very small quantities of salinomycin in the range of from about 0.2 to 0.8 milligrams are effective for increasing coronary flow or in cases of administration to subjects having a relatively low body weight, unit dosages for enhancing the contractile force of mammalian heart muscle are usually from about 0.5 milligrams to 5 milligrams. One-half to two milligrams appears optimum per unit dose. It is only necessary that salinomycin constitute an effective amount, i.e., such that a suitable effective dosage will be obtained, consistent with the dosage form employed. Obviously, several unit dosage forms may be administered at about the same time.

Accordingly, in the practice of the present invention salinomycin or a pharmaceutically acceptable salt of salinomycin or a water soluble lyophylized salinomycin - human serum albumen preparation is useful in increasing coronary flow when administered in an effective non-toxic dose of from about 0.2 milligram to 0.8 milligram and is useful in enhancing the contractile force of mammalian heart muscle when administered in an effective non-toxic dose of from about 0.5 milligram to two milligrams.

Salinomycin is non-toxic within the effective dose range as evidenced by the $LD_{50}$ expressed in mg/kg in animals. Thus, by oral administration the $LD_{50}$ of salinomycin is 125 mg/kg in chickens and 10 mg/kg in dogs.

We claim:

1. The method of increasing the contractility of mammalian heart muscle in a warm blooded mammal which comprises administering an effective non-toxic dose of salinomycin or the pharmaceutically acceptable sodium or potassium salt thereof.

2. The method of claim 1 wherein the effective non-toxic dose is from about 0.5 milligrams to 5.0 milligrams.

3. The method of claim 1 wherein the effective non-toxic dose is administered orally.

4. The method of claim 1 wherein the effective non-toxic dose is administered parenterally.

5. The method of increasing the contractility of mammalian heart muscle in a warm blooded mammal which comprises administering an effective non-toxic dose of a water soluble lyophilized salinomycin - human serum albumin preparation.

6. The method of increasing the coronary flow in a warm blooded mammal which comprises administering an effective non-toxic dose of salinomycin or the pharmaceutically acceptable sodium or potassium salt thereof.

7. The method of claim 6 wherein the effective non-toxic dose is from about 0.2 milligrams to 0.8 milligrams.

8. The method of claim 6 wherein the effective non-toxic dose is administered orally.

9. The method of claim 6 wherein the effective non-toxic dose is administered parentially.

10. The method of increasing the coronary flow in a warm blooded animal which comprises administering an effective dose of a water soluble lyophylized salinomycin - human serum albumin preparation.

11. A composition for increasing the contractility of mammalian heart muscle comprising a water soluble lyophylized salinomycin - human serum albumin preparation and a pharmaceutically acceptable carrier selected from water or saline.

12. A composition for increasing coronary flow comprising a water soluble lyophylized salinomycin - human serum albumin preparation and a pharmaceutically acceptable carrier selected from water or saline.

* * * * *